United States Patent [19]

Miyata et al.

[11] Patent Number: 4,749,689

[45] Date of Patent: Jun. 7, 1988

[54] HEMOSTATIC AGENT COMPOSED OF COLLAGEN/GELATIN AND PROTAMINE

[75] Inventors: Teruo Miyata, Tokyo; Kazuhiko Kodaira, Mitaka; Masayasu Furuse, Sagamihara; Yasuharu Noishiki, Tottori, all of Japan

[73] Assignee: Koken Co., Ltd., Tokyo, Japan

[21] Appl. No.: 87,966

[22] Filed: Aug. 17, 1987

Related U.S. Application Data

[62] Division of Ser. No. 798,969, Nov. 18, 1985, abandoned.

[30] Foreign Application Priority Data

Nov. 19, 1984 [JP] Japan ................................ 59-242472

[51] Int. Cl.$^4$ ...................... A61K 37/08; A61L 15/01; A61L 17/00; C08L 89/06
[52] U.S. Cl. ................................. 514/21; 514/8; 530/354; 530/356; 604/368; 128/DIG. 8; 128/325; 128/335.5
[58] Field of Search ...................... 514/21, 8; 530/354, 530/356; 604/368; 128/DIG. 8, 325, 335.5

[56] References Cited

U.S. PATENT DOCUMENTS

| | | | |
|---|---|---|---|
| 2,584,093 | 1/1952 | Pennell et al. | 424/92 |
| 3,717,469 | 2/1973 | Slonimsky et al. | 530/354 X |
| 3,742,955 | 7/1973 | Battista et al. | 128/334 |
| 4,140,537 | 2/1979 | Luck et al. | 530/356 X |
| 4,215,200 | 7/1980 | Miyata et al. | 530/356 X |
| 4,223,984 | 9/1980 | Miyata et al. | 530/356 X |
| 4,260,228 | 4/1981 | Miyata | 530/356 |
| 4,268,131 | 5/1981 | Miyata et al. | 530/356 X |
| 4,271,070 | 6/1981 | Miyata et al. | 530/356 |
| 4,374,830 | 2/1983 | Schneider | 514/21 |
| 4,424,208 | 1/1984 | Wallace et al. | 530/356 X |
| 4,557,764 | 12/1985 | Chu | 530/356 X |
| 4,565,580 | 1/1986 | Miyata et al. | 530/356 X |
| 4,582,640 | 4/1986 | Smestad et al. | 530/356 |
| 4,592,864 | 6/1986 | Miyata et al. | 530/356 |

FOREIGN PATENT DOCUMENTS 92414 10/1983 European Pat. Off. .

OTHER PUBLICATIONS

Chem. Abstracts, 32, 62668, Pedersen, 1938.
Chem. Abstracts, 97, 223011h, Zimmermann et al., 1982.
Coln, et al., (1983), Hemostatic Agents in Splenic Lacerations, American Journal of Surgery 145, pp. 256–259.
Abbott, et al., (1975), The Effectiveness and Mechanism of Collagen-Induced Topical Hemostasis; *Surgery*, vol. 78, No. 6, pp. 723–729.

*Primary Examiner*—Howard E. Schain
*Attorney, Agent, or Firm*—Sherman and Shalloway

[57] ABSTRACT

This invention relates to a hemostatic agent used in surgical operations, which can be produced in two ways: one blending collagen/gelatin with protamine, the other blending collagen/gelatin with protamine and a bi-functional cross-linking agent so as to make said collagen/gelatin have a covalent bond with said protamine. The produced hemostatic agent can stop bleeding within far less time than a conventional hemostatic agent made out of pure collagen.

9 Claims, No Drawings

HEMOSTATIC AGENT COMPOSED OF COLLAGEN/GELATIN AND PROTAMINE

This application is a division of application Ser. No. 798,969, filed Nov. 18, 1985, now abandoned.

This invention relates to a hemostatic agent intended to stop bleeding by surgical operations or injuries, which, therefore, has a wide application in the surgical field.

In surgical operations, to stop bleeding from capillaries is as crucially important as to stop bleeding by ligation in order to conduct operations skillfully shortening the time as much as possible. From this point of view, the development of a hemostatic agent that can quickly and simply stop bleeding to which ligation cannot apply has long been awaited.

To put it ideally, an administered hemostatic agent should have a good affinity with living tissues and can be assimilated thereto in the long run. Meantime, it has been well known that collagen, an essential component of connective tissues, is concerned with coagulation of blood. Particularly, collagen is known to have a function of first activating thrombocyte so as to stop bleeding and then inducing it to form thrombus finally. Collagen works such that hemostatic agents have so far been produced from collagen only by making use of that advantageous function. For all that, actually it takes so much time to stop bleeding in operations that a hemostatic agent capable of stopping bleeding in less time is desired strongly.

Accordingly, it is an object of this invention to provide a hemostatic agent in which the excellent action of collagen is utilized much more so as to stop bleeding in a very short period of time. That is, the object of this invention is accomplished by a hemostatic agent produced by blending collagen/gelatin with protamine or a hemostatic agent produced by blending collagen/gelatin with protamine and a bi-functional cross-linking agent so as to make said collagen/gelatin have a covalent bond with said protamine. In more detail, the former is a hemostatic mixture composed of collagen/gelatin and protamine, whereas the latter is a hemostatic agent in which collagen/gelatin has a covalent bond with protamine by means of a cross-linking agent.

Referring now to collagen employed in this invention, it includes atelocollagen extracted from dermis of a calf by the use of a proteolytic enzyme (e.g., pepsin) except for collagenase, water-insoluble collagen purified from tendon or placenta, gelatin, a denatured product of collagen and the like, for example.

Recently, collagen of which teropeptide is removed is called atelocollagen. The antigenicity of collagen is attributed largely to the presence of telopeptide in its molecule; therefore, atelocollagen, having lost telopeptide, has almost no such antigenicity that it is most suitable for a material to produce hemostatic agents. Moreover, the reason that a water-insoluble collagen is "insoluble" comes from the fact that an inter-molecular telopeptide cross-link is present at every end of its molecule; accordingly, when telopeptide is attacked by pepsin, a proteolytic enzyme, the cross-link is broken and water-soluble atelocollagen is formed. In this connection, atelocollagen is also obtained by treating a water-insoluble collagen with pepsin after extracting by a dilute acid solution or an aqueous solution containing neutral salts.

Protamine employed in this invention includes a group of basic nuclear proteins, collectively called protamine, such as clupeine, salmine, iridin, tinin, mugiline, sterin, scombrine, siprinine, lacustrine, which are isolated from fish sperm nucleus, gallin, which is isolated from fowl sperm nucleus, etc. Likewise, this invention can employ proteins containing a histone-type protein which is a homologue of protamine.

Protamine forms a salt-like complex in conjunction with inorganic acids or organic acids; that is, it gives hydrochloride, sulfate, carbonate, nitrate, acetate, phosphate, etc.; therefore, these salt-like complex dissolve in water. This invention prefers to use such salt-like complex, among which protamine sulfate and protamine hydrochloride are more desirable than others.

According to this invention 0.001–2 g of protamine is mixed into 1 g of collagen; more preferably, 0.01–1 g of protamine is mixed into 1 g of collagen.

Also, glutaraldehyde, hexamethylene diisocyanate and the like are used as a bi-functional cross-linking agent to cause collagen and protamine to have a covalent bond. More particularly, in order to form a covalent bond between them, they are immersed in and made to react with a solution containing 0.001–5%, more preferably 0.1–2% of the bi-functional cross-linking agent for 10 minutes–24 hours at pH of neutrality and over.

As seen from the above, according to this invention, in order to produce a hemostatic agent, it is possible to get collagen and protamine to have a covalent bond or merely mix them together, by which physical properties of the produced hemostatic agent, such as strength, specific gravity, viscosity, etc. can be controlled at manufacturer's disposal; besides, a variety of treatment can be applied to the product.

The hemostatic agent of this invention, once produced, can be put to practical use in various forms, not only crushed into powder but also molded into sponge, casted into film, spun into filament, prepared into solution or solution in which hemostatic agent is dispersed in the fibrillar form.

As mentioned earlier, collagen is deeply involved in the activation of thrombocyte accounting for the primary hemostatic action, which then causes adhesion and coagulation reaction in thrombocyte and finally forms thrombus to stop bleeding. The adhesion reaction in thrombocyte is regarded as being caused by guanidino radicals on strongly basic arginine residues of collagen. On the other hand, protamine, because of being a nuclear protein that contains plenty of arginine residues, is strongly basic and has a positive charge when made neutral; therefore, thrombocyte, having a negative charge, is activated by such protamine upon adhering thereto.

For the above reasons, the combinative use of collagen and protamine increases guanidino radicals because guanidino radicals on arginine radicals of collagen, which are thought to bring about the adhesion reaction, and guanidino radicals on arginine radicals of protamine are added together; what is more, it prompts the adhesion reaction in thrombocyte and enhances the hemostatic effect very much.

Since protamine is widely used therapeutically as a neutralizing agent for an acid mucopolysaccharide called heparin, which is an inhibitor of endogenous blood coagulation, the hemostatic agent of this invention particularly brings forth a remarkable hemostatic effect in operations where heparin is used as an antithrombotic agent. After all, compared with a conventional hemostatic agent composed pure collagen, the hemostatic agent of this invention can reduce the time until bleeding stops to a maximum extent.

[EXAMPLE 1]

Some fresh dermis of a calf was crushed into very small pieces; they were rinsed in a 0.1 mole sodium acetate solution repeatedly and finally rinsed in water. After that, they were subjected to an extraction treatment by the use of a 0.5 mole acetic acid solution. Residual water-insoluble collagen was filtered out by means of a glass filter. One hundred grams of the insoluble collagen were taken in a moistened condition, to which 1 l of a 0.5 mole acetic acid solution and 0.1 g of pepsin were added; stirring was kept for 3 days at 20° C. The water-insoluble collagen dissolved and left a viscous, pepsin-solubilized collagen (i.e., atelocollagen).

After the atelocollagen was filtered by means of a glass filter, a sodium hydroxide solution was added to the filtrate so as to adjust its pH to 7.5. As a result, a fibrous precipitate appeared, which was then centrifuged and rinsed with distilled water three times. Atelocollagen was thus produced.

Mixed into a 2% atelocollagen solution acidified (to pH 3) by hydrochloric acid was 0.1 g of protamine sulfate per 1 g of the atelocollagen. While the mixture was being stirred by means of a homogenizer, its pH was adjusted to 8.0 by a 0.1N sodium hydroxide solution. A lump of sponge was produced by freeze-drying the mixture.

The sponge was next immersed in a methanol solution containing 2% hexamethylene diisocyanate in order to introduce a cross-link. After rinsed well in water to remove free protamine, the sponge was freeze-dried again. At this moment, the protamine has a covalent bond with the atelocollagen, so that free protamine is not contained in the sponge, a hemostatic agent of this invention.

[EXAMPLE 2]

Some gelatin was dissolved in water at 60° C. so as to give a 2% gelatin solution. After the solution was cooled to room temperatures, 0.1 g of protamine sulfate was dissolved in it per 1 g of gelatin. The mixture was freeze-dried and molded into a piece of sponge which was then soaked in a methanol solution containing 2% hexamethylene diisocyanate in order to introduce a covalent bond between protamine and gelatin. After that, the same treatment as in Example 1 was carried out to give a spongy hemostatic agent in which gelatin has a covalent bond with protamine.

[EXAMPLE 3]

Some fresh tendon of a cow was rinsed well in water and then broken into fibrils by a mixer. They were rinsed in water many times and lightly dehydrated. One liter of a phosphate buffer solution (pH=7.0) was added to 100 g of the moistened fibrils and then 0.13 g of pancreatin was added. The mixture was kept standing at room temperatures overnight.

After that, it was rinsed in water many times and dehydrated in order to remove alien proteins barring collagen. The collagen was soaked in a 1% $NaHCO_3$ solution, rinsed in water and dehydrated. Remaining water was removed stepwise by using 70%, 80%, 90% and 100% ethanol. Finally, the water-insoluble collagen, obtained from a cow's tendon, was dried in the air.

An amount of the insoluble collagen was dispersed in water so as to make its consistency 2% and the pH of the disperse solution was adjusted to 3 by a 1N hydrochloric acid solution. Added to 1 g of the collagen was 0.1 g of protamine sulfate. After that, the same treatment as in Example 1 was conducted in order to obtain a piece of sponge in which protamine and the insoluble collagen have a covalent bond.

[EXAMPLE 4]

An acid 10% atelocollagen solution was extruded from a fine nozzle into a NaCl saturated solution so as to give a filament, which was then rolled, dried in a dryer and taken up. Thus, a wet-spun filament which contained collagen molecule oriented to the fiber axis was obtained. The filament, 1–5 denier in thickness, was soaked in a 1% protamine sulfate solution in order to absorb protamine and then soaked in a 1% glutaraldehyde solution in order to get the absorbed protamine form a covalent bond with collagen molecule. After rinsed well in water to remove free protamine, the filament was dried in the air. A filamentary hemostatic agent of this invention was thus produced.

[EXAMPLE 5]

A HCl-acidified 3% atelocollagen solution was prepared; 0.1 g of protamine sulfate was added per 1 g of the collagen. The pH of the solution was adjusted to 10–11 by the addition of a 1N NaOH solution in order to cause collagen and protamine to form precipitate. The solution was centrifuged to collect the precipitate and methanol was used to remove water from it. A methanol solution containing 2% hexamethylene diisocyanate was added to it to form a covalent bond between the atelocollagen and the protamine.

The resulting product was rinsed well in methanol and dried in the air. It was rinsed well in water again to remove free protamine and water was removed by methanol. The product was dried in the air and crushed into pieces. A powdery hemostatic agent of this invention was thus obtained.

[EXAMPLE 6]

One hundred milli-liters of a solution containing 0.03 mole acetic acid were added to 1 g of the powdery product obtained in Example 5 in order to swell it. A homogenizer was employed to disperse the product in the solution in the fibrillar form. A hemostatic agent in the form of a disperse solution was thus obtained.

[EXAMPLE 7]

One hundred milli-liters of a solution containing 0.03 mole acetic acid were added to 0.5 g of atelocollagen in order to dissolve it. The solution thus prepared was put under reduced pressure to remove bubbles, spread over a flat acrylate plate at a thickness of 5 mm and dried in the air by sending a faint air stream. After dried up, a film produced on the acrylate plate was peeled off therefrom. Thus, a filmy hemostatic agent of this invention composed of collagen and protamine was obtained.

A variety of hemostatic agents of this invention, obtained in the above examples, were subjected to an animal experiment to ascertain their hemostatic effect. For the purpose of comparison, the surface of a dog's spleen was sliced off by a knife and the time until bleeding stopped by applied hemostatic agents was measured. A spongy hemostatic agent that does not contain protamine but collagen only took 158±68 seconds to stop bleeding, while the spongy hemostatic agent of Example 1 took 66±26 seconds, reducing the time to stop bleeding more than a half.

Similarly, the gelatin hemostatic agent of Example 2, having a covalent bond with protamine, reduced the time to stop bleeding more than a half, compared with a hemostatic agent of pure gelatin.

Other than the two examples, the collagen sponge of Example 3, the collagen filament of Example 4, the collagen powder of Example 5, the collagen fibril-dispersed solution of Example 6 and the collagen film of Example 7 all reduced the time to stop bleeding more than a half, compared with corresponding 100% collagen hemostatic agents.

Accordingly, it was ascertained that the hemostatic agent of this invention is extremely effective to staunch bleeding.

We claim:

1. A method of controlling bleeding comprising applying to a bleeding tissue a hemostatic agent composed of collagen or gelatin and protamine.

2. The method of claim 1 wherein said collagen or gelatin and protamine are covalently bonded together by a bifunctional crosslinking agent.

3. The method of claim 1 wherein said hemostatic agent is in the form of a sponge, a powder, a film or a dispersed solution.

4. The method of claim 1 wherein said hemostatic agent comprises collagen and protamine.

5. The method of claim 4 wherein said collagen is atelocollagen.

6. The method of claim 2 wherein said bifunctional crosslinking agent is glutaraldehyde or hexamethylene diisocyanate.

7. The method of claim 1 wherein said protamine is protamine sulfate or protamine hydrochloride.

8. The method of claim 1 wherein said bleeding is the result of injury or surgical operation.

9. The method of claim 8 wherein said bleeding is the result of a splenic injury and said hemostatic agent is applied directly to the splenic tissue.

* * * * *